(12) United States Patent
Morisson-Iveson et al.

(10) Patent No.: US 8,323,619 B2
(45) Date of Patent: Dec. 4, 2012

(54) CONTRAST AGENTS

(75) Inventors: Veronique Morisson-Iveson, Amersham (GB); Duncan George Wynn, Amersham (GB)

(73) Assignee: GE Healthcare AS, Oslo (NO)

( * ) Notice: Subject to any disclaimer, the term of this patent is extended or adjusted under 35 U.S.C. 154(b) by 391 days.

(21) Appl. No.: 12/739,989

(22) PCT Filed: Nov. 6, 2008

(86) PCT No.: PCT/EP2008/065042
§ 371 (c)(1),
(2), (4) Date: Apr. 27, 2010

(87) PCT Pub. No.: WO2009/060021
PCT Pub. Date: May 14, 2009

(65) Prior Publication Data
US 2010/0233097 A1 Sep. 16, 2010

(30) Foreign Application Priority Data

Nov. 7, 2007 (NO) .................................... 20075677

(51) Int. Cl.
*A61K 49/04* (2006.01)
(52) U.S. Cl. ...................... 424/9.4; 424/9.452
(58) Field of Classification Search ............... 424/9.452
See application file for complete search history.

(56) References Cited

U.S. PATENT DOCUMENTS

2004/0198834 A1 10/2004 Lasser

OTHER PUBLICATIONS

Database Registry CAS; 154361-55-4 RN Mar. 15, 1994.
EP2008/065042 ISRWO Dated Jan. 29, 2009.

*Primary Examiner* — Michael G Hartley
*Assistant Examiner* — Melissa Perreira

(57) ABSTRACT

Compounds of formula (I) $R^A$—CO—$N(R^2)$—$(CR^1{}_2)_n$—$N(R^5)$—$R^B$ and salts or optical active isomers thereof, wherein each $R^1$ independently are the same or different and denotes a hydrogen atom, a hydroxyl group, a $C_1$ to $C_4$ straight of branched alkyl group or a $C_1$ to $C_4$ straight of branched oxyalkyl group; $R^2$ denotes a hydrogen atom or a $C_1$ to $C_4$ straight of branched alkyl group; $R^5$ independently are the same or different and denotes a acyl moiety; $R^A$ and $R^B$ independently are the same or different and denote a triiodinated phenyl group, preferably a 2,4,6-triiodinated phenyl group further substituted by two groups $R^3$ in the 3 and 5 positions wherein each $R^3$ are the same or different and denote a hydrogen atom or a non-ionic hydrophilic moiety, provided that at least one $R^3$ group in the compound of formula (I) is a hydrophilic moiety; and n denotes a positive integer of 1 to 6. The invention also relates to the use of such diagnostic compositions as contrast agents in diagnostic imaging and in particular in X-ray imaging, and to contrast media containing such compounds.

17 Claims, No Drawings

CONTRAST AGENTS

This application is a filing under 35 U.S.C. 371 of international application number PCT/EP2008/065042, filed Nov. 6, 2008, which claims priority to Norwegian application number 20075677 filed Nov. 7, 2007, the entire disclosure of which is hereby incorporated by reference.

TECHNICAL FIELD OF THE INVENTION

The present invention relates to a class of compounds and to diagnostic compositions containing such compounds where the compounds are iodine containing compounds. More specifically the iodine containing compounds are chemical compounds containing two linked iodinated phenyl groups.

The invention also relates to the use of such diagnostic compositions as contrast agents in diagnostic imaging and in particular in X-ray imaging, and to contrast media containing such compounds.

DESCRIPTION OF RELATED ART

All diagnostic imaging is based on the achievement of different signal levels from different structures within the body. Thus in X-ray imaging for example, for a given body structure to be visible in the image, the X-ray attenuation by that structure must differ from that of the surrounding tissues. The difference in signal between the body structure and its surroundings is frequently termed contrast and much effort has been devoted to means of enhancing contrast in diagnostic imaging since the greater the contrast between a body structure and its surroundings the higher the quality of the images and the greater their value to the physician performing the diagnosis. Moreover, the greater the contrast the smaller the body structures that may be visualized in the imaging procedures, i.e. increased contrast can lead to increased spatial resolution.

The diagnostic quality of images is strongly dependent on the inherent noise level in the imaging procedure, and the ratio of the contrast level to the noise level can thus be seen to represent an effective diagnostic quality factor for diagnostic images.

Achieving improvement in such a diagnostic quality factor has long been and still remains an important goal. In techniques such as X-ray, magnetic resonance imaging (MRI) and ultrasound, one approach to improving the diagnostic quality factor has been to introduce contrast enhancing materials formulated as contrast media into the body region being imaged.

Thus in X-ray early examples of contrast agents were insoluble inorganic barium salts which enhanced X-ray attenuation in the body zones into which they distributed. For the last 50 years the field of X-ray contrast agents has been dominated by soluble iodine containing compounds. Commercial available contrast media containing iodinated contrast agents are usually classified as ionic monomers such as diatrizoate (marketed e.g. under the trade name Gastrografen™), ionic dimers such as ioxaglate (marketed e.g. under the trade name Hexabrix™), nonionic monomers such as iohexol (marketed e.g. under the trade name Omnipaque™), iopamidol (marketed e.g. under the trade name Isovue™), iomeprol (marketed e.g. under the trade name Iomeron™) and the non-ionic dimer iodixanol (marketed under the trade name and Visipaque™).

The most widely used commercial non-ionic X-ray contrast agents such as those mentioned above are considered safe. Contrast media containing iodinated contrast agents are used in more that 20 millions of X-ray examinations annually in the USA and the number of adverse reactions is considered acceptable. However, since a contrast enhanced X-ray examination will require up to about 200 ml contrast media administered in a total dose, there is a continuous drive to provide improved contrast media.

The utility of the contrast media is governed largely by its toxicity, by its diagnostic efficacy, by adverse effects it may have on the subject to which the contrast medium is administered, and by the ease of storage and ease of administration. Since such media are conventionally used for diagnostic purposes rather than to achieve direct therapeutic effect, it is generally desirable to provide media having as little as possible effect on the various biological mechanisms of the cells or the body as this will lead to lower toxicity and lower adverse clinical effect. The toxicity and adverse biological effects of a contrast medium are contributed to by the components of the formulation medium, e.g. the solvent or carrier as well as the contrast agent itself and its components such as ions for the ionic contrast agents and also by its metabolites.

The major contributing factors to the toxicity of the contrast medium are identified as the chemotoxicity of the contrast agent, the osmolality of the contrast medium and the ionic composition or lack thereof of the contrast medium.

Desirable characteristics of an iodinated contrast agent are low toxicity of the compound itself (chemotoxicity), low viscosity of the contrast medium wherein the compound is dissolved, low osmolality of the contrast medium and a high iodine content (frequently measured in g iodine per ml of the formulated contrast medium for administration). The iodinated contrast agent must also be completely soluble in the formulation medium, usually an aqueous medium, and remain in solution during storage.

The osmolalities of the commercial products, and in particular of the non-ionic compounds is acceptable for most media containing dimers and non-ionic monomers although there is still room for improvement. In coronary angiography for example, injection into the circulatory system of a bolus dose of contrast medium has caused severe side effects. In this procedure contrast medium rather than blood flows through the system for a short period of time, and differences in the chemical and physiochemical nature of the contrast medium and the blood that it replaces can cause undesirable adverse effects such as arrhythmias, QT prolongation and reduction in cardiac contractive force. Such effects are seen in particular with ionic contrast agents where osmotoxic effects are associated with hypertonicity of the injected contrast medium. Contrast media that are isotonic or slightly hypotonic with the body fluids are particularly desired. Low osmolar contrast media have low renal toxicity which is particularly desirable. The osmolality is a function of the number of particles per volume unit of the formulated contrast medium.

In patients with acute renal failure, nephropathy induced by contrast medium remains one of the most clinically important complications of the use of iodinated contrast medium. Aspelin, P et al, The New England Journal of Medicine, Vol. 348:491-499 (2003) concluded that nephropathy induced by contrast medium may be less likely to develop in high risk patients when iodixanol is used rather than a low-osmolar, non-ionic contrast medium.

The part of the patient population considered as high risk patients is increasing. To meet the need for continuous improvement of in vivo X-ray diagnostic agents for the entire patient population, there is a continuous drive in finding X-ray contrast agents that has improved properties, also with regards to contrast induced nephrotoxicity (CIN).

To keep the injection volume of the contrast media as low as possible it is highly desirable to formulate contrast media with high concentration of iodine/ml, and still maintain the osmolality of the media at a low level, preferably below or close to isotonicity. The development of non-ionic monomeric contrast agents and in particular non-ionic bis(triiodophenyl) dimers such as iodixanol (EP patent 108638) has provided contrast media with reduced osmotoxicity allowing contrast effective iodine concentration to be achieved with hypotonic solution, and has even allowed correction of ionic imbalance by inclusion of plasma ions while still maintaining the contrast medium Visipaque™ at the desired osmolality (WO 90/01194 and WO 91/13636).

The X-ray contrast media at commercial high iodine concentration have relative high viscosity, ranging from about 15 to about 60 mPas at ambient temperature. Generally, contrast media where the contrast enhancing agent is a dimer has higher viscosity than the corresponding contrast media where the contrast enhancing agent is the monomer corresponding to the dimer. Such high viscosities may pose problems to the administrators of the contrast medium, requiring relatively large bore needles or high applied pressure, and are particularly pronounced in pediatric radiography and in radiographic techniques which require rapid bolus administration, e.g. in angiography.

X-ray contrast media containing a chemical compound as the active pharmaceutical ingredient(s) having two triiodinated phenyl groups linked by a linking group are usually referred to as dimeric contrast agents or dimers. During the years a wide variety of iodinated dimers have been proposed. Relevant patent publications comprises EP 1186305, EP 686046, EP108638, EP 0049745, EP 0023992, WO 2003080554, WO2000026179, WO 1997000240, WO 9208691, U.S. Pat. No. 3,804,892, U.S. Pat. No. 4,239,747, U.S. Pat. No. 3,763,226, U.S. Pat. No. 3,763,227 and U.S. Pat. No. 3,678,152. At this time, one contrast medium having an iodinated non-ionic dimer as the active pharmaceutical ingredient is one the market, the product Visipaque™ containing the compound iodixanol. The compound Hexabrix™, containing the ionic dimeric compound ioxaglic acid is also on the market.

WO92/08691 of Dibra and Bracco proposes symmetrical or asymmetrical 1,3-bis-[3-(mono- or poly-hydroxy)acylamino-5-(mono- or poly-hydroxyalkyl)aminocarbonyl-2,4,6-triiodo-benzoyl-amino]-hydroxy or hydroxyalkyl-propanes and exemplifies a number of these compounds. Tables 1 and 2 provide some test results of the compounds of Examples 1 and 10 of the patent specification. However, none of the compounds prepared in WO92/08691 are developed and brought to the market.

Hence there still exists a desire to develop contrast agents that solves one or more of the problems discussed above. Such agents should ideally have improved properties over the soluble iodine containing compounds on the market in one or more of the following properties: renal toxicity, osmolality, viscosity, solubility, injection volumes/iodine concentration and attenuation/radiation dose and any additional adverse effect known or discovered for such iodinated compounds.

SUMMARY OF THE INVENTION

The present invention provides compounds useful as contrast media having desired properties with regards to at least one of the criteria mentioned above, and in particular to renal toxicity, osmolality, viscosity and solubility. The contrast media comprises iodine containing contrast enhancing compounds where iodine containing compounds are chemical compounds containing two iodinated phenyl groups linked by an unsymmetrical linker. The iodine containing contrast enhancing compounds can be synthesized from commercially available and relatively inexpensive starting materials.

DETAILED DESCRIPTION OF THE INVENTION

The new compounds of the invention, their use as X-ray contrast agents, their formulation and production are specified in the attached claims and in the specification hereinafter.

The contrast enhancing compounds are synthetic chemical compounds of formula (I)

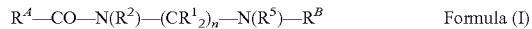

$$R^A\text{—CO—N}(R^2)\text{—}(CR^1{}_2)_n\text{—N}(R^5)\text{—}R^B \qquad \text{Formula (I)}$$

and salts or optical active isomers thereof,
wherein
each $R^1$ independently are the same or different and denotes a hydrogen atom, a hydroxyl group, a $C_1$ to $C_4$ straight of branched alkyl group or a $C_1$ to $C_4$ straight of branched oxyalkyl group;
$R^2$ denotes a hydrogen atom or a $C_1$ to $C_4$ straight of branched alkyl group;
$R^5$ denotes an acyl moiety;
$R^A$ and $R^B$ independently are the same or different and denote a triiodinated phenyl group, preferably a 2,4,6-triiodinated phenyl group further substituted by two groups $R^3$ in the 3 and 5 positions wherein each $R^3$ are the same or different and denote a hydrogen atom or a non-ionic hydrophilic moiety, provided that at least one $R^3$ group in the compound of formula (I) is a hydrophilic moiety; and
n denotes a positive integer of 1 to 6.

In formula (I) above, each $R^1$ group preferably denote hydrogen atoms and/or a hydroxyl groups, more preferred the $R^1$ groups are different, and most preferred one $R^1$ denotes a hydrogen atom while the other $R^1$ denotes hydroxyl group.

The $R^2$ group preferably denote a hydrogen atom or a methyl group, most preferred a hydrogen atom.

The $R^5$ group preferably denote a group of formula —CO—$R^4$ where $R^4$ denotes a hydrogen atom or a $C_1$ to $C_4$ straight of branched alkyl group optionally substituted by 1 to 4 hydroxyl moieties. More preferred, $R^5$ denotes one of the acyl groups of formula —CHO, —COCH$_3$, —COCH$_2$—OH and —CO—CHOH—CH$_2$—OH, and most preferred $R^5$ denotes formyl and acetyl residues.

n is preferably an integer of 2 to 5, most preferably n is 3.

Each of the two iodinated $R^A$ and $R^B$ groups in the compound of formula (I) can be the same or different and preferably denote a 2,4,6-triiodinated phenyl group, further substituted by two groups $R^3$ in the remaining 3 and 5 positions in the phenyl moiety.

More preferred the $R^A$ and $R^B$ groups are different, each of them being residues of amino phthalic acids substituted by iodine in the 2,4,6 positions, where $R^A$ is linked to the bridging element —CO—N($R^2$)—(CR$^1{}_2$)$_n$—N($R^5$)— through the carbonyl group and $R^A$ further contains one group $R^3$ of the formula —N($R^9$)—CO—$R^6$ while the other $R^3$ group is of formula —CO—N($R^7R^8$). $R^B$ is linked to the bridging element —CO—N($R^2$)—(CR$^1{}_2$)$_n$—N($R^5$)— through the amine group and further contains two $R^3$ of formula —CO—N($R^7R^8$).

The general and specific meanings of $R^6$, $R^7$, $R^8$ and $R^9$ will be evident from the definition of the moieties $R^3$ below.

The non-ionic hydrophilic moieties $R^3$ may be any of the non-ionizing groups conventionally used to enhance water solubility. Hence, the $R^3$ substituents may be the same or different and shall preferably all denote a non-ionic hydrophilic moiety comprising esters, amides and amine moieties, optionally further substituted by a straight chain or branched chain $C_{1-10}$ alkyl groups, preferably $C_{1-5}$ alkyl groups, where the alkyl groups also may have one or more $CH_2$ or CH moieties replaced by oxygen or nitrogen atoms. The $R^3$ substituents may also further contain one or more groups selected from oxo, hydroxyl, amino or carboxyl derivative, and oxo substituted sulphur and phosphorus atoms. Each of the straight or branched alkyl groups preferably contains 1 to 6 hydroxy groups and more preferably 1 to 3 hydroxy groups. Therefore, in a further preferred aspect, the $R^3$ substituents are the same or different and are polyhydroxy $C_{1-5}$ alkyl, hydroxyalkoxyalkyl with 1 to 5 carbon atoms and hydroxy-polyalkoxyalkyl with 1 to 5 carbon atoms, and are attached to the iodinated phenyl group via an amide or a carbamoyl linkage.

The $R^3$ groups of the formulas listed below are particularly preferred:
—CONH—$CH_2$—$CH_2$—OH
—CONH—$CH_2$—CHOH—$CH_2$—OH
—CON($CH_3$)$CH_2$—CHOH—$CH_2$OH
—CONH—CH—($CH_2$—OH)$_2$
—CON—($CH_2$—$CH_2$—OH)$_2$
—$CONH_2$
—$CONHCH_3$
—$NHCOCH_2OH$
—N($COCH_3$)H
—N($COCH_3$)$C_{1-3}$ alkyl
—N($COCH_3$)— mono, bis or tris-hydroxy $C_{1-4}$ alkyl
—N($COCH_2OH$)— hydrogen, mono, bis or tris-hydroxy $C_{1-4}$ alkyl
—N(CO—CHOH—$CH_2OH$)— hydrogen, mono, bis or trihydroxylated $C_{1-4}$ alkyl
—N(CO—CHOH—CHOH—$CH_2OH$)— hydrogen, mono, bis or trihydroxylated $C_{1-4}$ alkyl
—N($COCH_2OH$)$_2$
—CON($CH_2$—CHOH—$CH_2$—OH)($CH_2$—$CH_2$—OH)
—CONH—C($CH_2$—OH)$_3$ and
—CONH—CH($CH_2$—OH)(CHOH—$CH_2$—OH).

More preferably the $R^3$ groups will be equal or different and denote one or more moieties of the formulas —CONH—$CH_2$—CHOH—$CH_2$—OH, —CON($CH_3$)$CH_2$—CHOH—$CH_2OH$, —CONH—CH—($CH_2$—OH)$_2$, —CON—($CH_2$—$CH_2$—OH)$_2$, —CON(CHOH—$CH_2$—OH)($CH_2$—$CH_2OH$), —NH—$COCH_2OH$, —NH—CO—CHOH—$CH_2OH$ and —NH—CO—CHOH—CHOH—$CH_2OH$.

Preferred structures are those of formula (II):

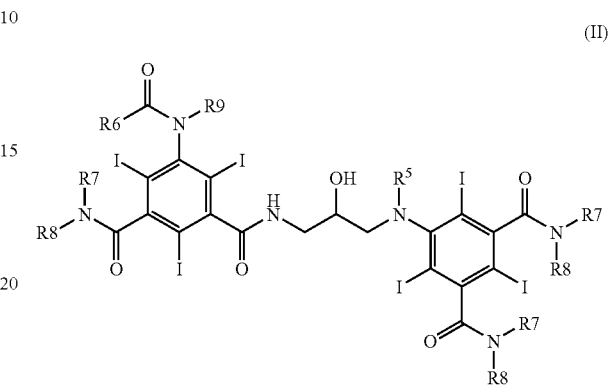

(II)

In formula (II), $R^6$ represents a moiety —$CH_2$—OH, —CHOH—$CH_2$—OH or CHOH—CHOH—$CH_2$—OH; $R^9$ represents a H, —$CH_3$, —$CH_2$—$CH_2$—OH or —$CH_2$—CH(OH)—$CH_2$—OH; and each of $R^7$ and $R^8$ are the same or different and represents H, —$CH_3$, —$CH_2$—$CH_2$—OH or —$CH_2$—CH(OH)—$CH_2$—OH and $R^5$ denotes a formyl or acetyl residue.

Even more preferably, $R^6$ represents a moiety —$CH_2$—OH or —CHOH—$CH_2$—OH; $R^9$ represents a hydrogen atom; and each of $R^7$ and $R^8$ are the same or different and represents a hydrogen atom, —$CH_2$—$CH_2$—OH or —$CH_2$—CH(OH)—$CH_2$—OH Thus, preferred structures according to the invention include the compounds of formula (IIIa) to (IIIe):

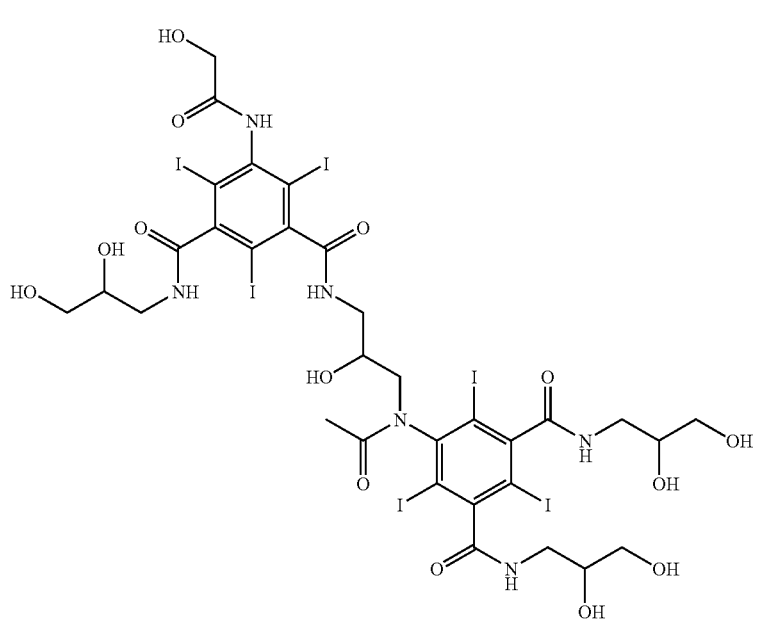

Formula (IIIa)

-continued
Formula (IIIb)
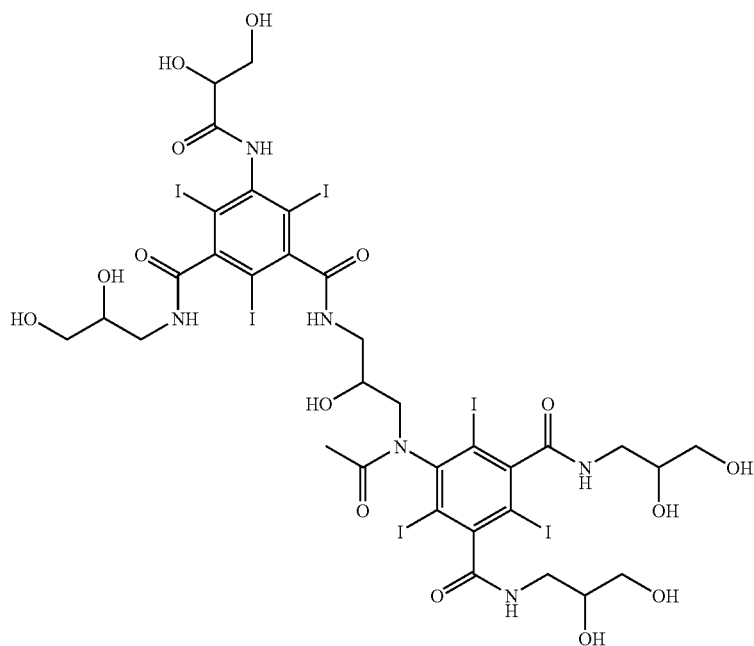
Formula (IIIc)
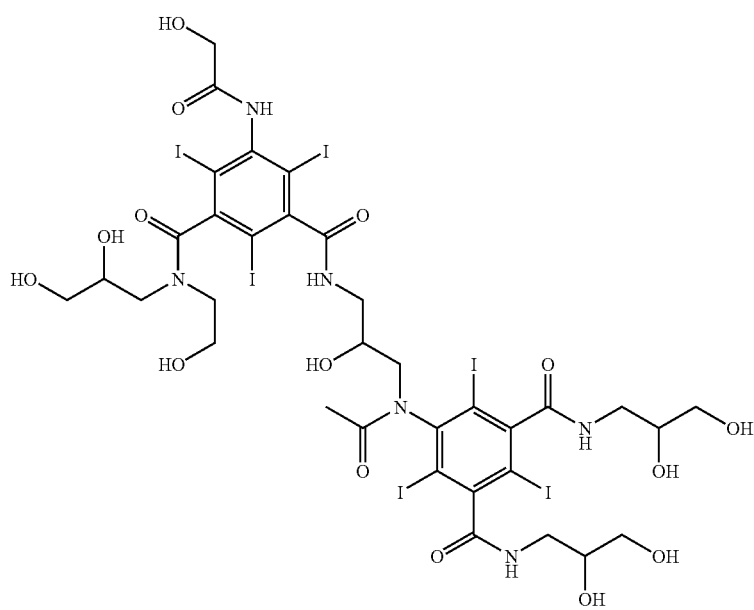

Formula (IIId)

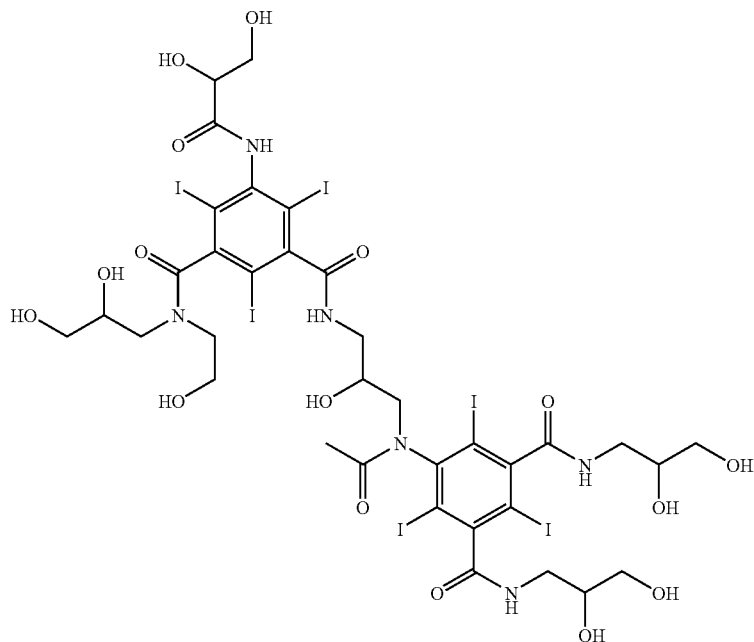

Formula (IIIe)

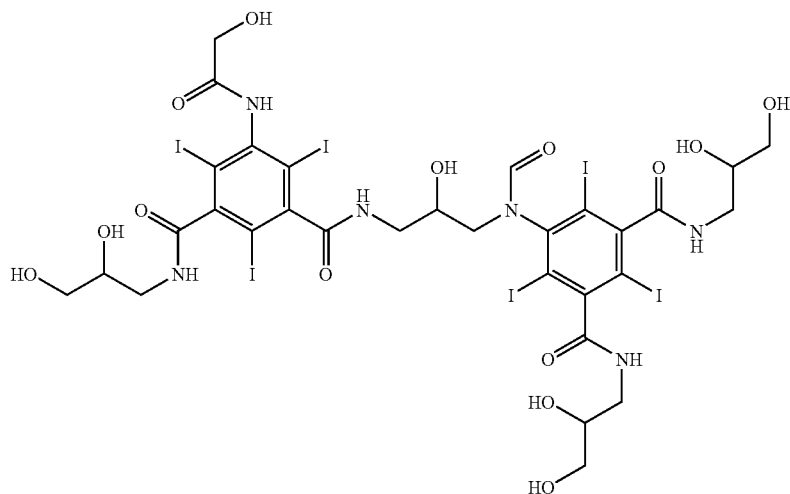

At an iodine concentration of 320 mg/ml, which is a common concentration for commercially available iodinated contrast media, the concentration of the compound of formula (I) will be approximately 0.42 M (Molar). The contrast medium will also be hypoosmolar at this iodine concentration, and this is an advantageous property with regards to the nephrotoxicity of the contrast medium. It is also possible to add electrolytes to the contrast medium to lower the cardiovascular effects as explained in WO 90/01194 and WO 91/13636.

Compounds of formula (I) also comprises optical active isomers and may exist in several isomeric forms due to chiral carbon atoms. In addition, the compounds exhibit exo/endo isomerism due to the restricted rotation of the amide bond caused by the proximity of the bulk iodine atom. Both enantiomerically pure products as well as mixtures of optical isomers are included.

The compounds of the invention may be used as contrast agents and may be formulated with conventional carriers and excipients to produce diagnostic contrast media.

Thus viewed from a further aspect the invention provides a diagnostic composition comprising a compound of formula (I) as described above together with at least one physiologically tolerable carrier or excipient, e.g. in aqueous solution for injection optionally together with added plasma ions or dissolved oxygen.

The contrast agent composition of the invention may be in a ready to use concentration or may be a concentrate form for dilution prior to administration. Generally compositions in a ready to use form will have iodine concentrations of at least 100 mg I/ml, preferably at least 150 mg I/ml, with concentrations of at least 300 mg I/ml, e.g. 320 mg I/ml being preferred. The higher the iodine concentration, the higher is the diagnostic value in the form of X-ray attenuation of the contrast media. However, the higher the iodine concentration the higher is the viscosity and the osmolality of the composition. Normally the maximum iodine concentration for a given contrast media will be determined by the solubility of the contrast enhancing agent, e.g. the iodinated compound, and the tolerable limits for viscosity and osmolality.

For contrast media which are administered by injection or infusion, the desired upper limit for the solution's viscosity at ambient temperature (20° C.) is about 30 mPas, however viscosities of up to 50 to 60 mPas and even more than 60 mPas can be tolerated. For contrast media given by bolus injection, e.g. in angiographic procedures, osmotoxic effects must be considered and preferably the osmolality should be below 1 Osm/kg $H_2O$, preferably below 850 mOsm/kg $H_2O$ and more preferably about 300 mOsm/kg $H_2O$.

With the compounds of the invention such viscosity, osmolality and iodine concentrations targets can be met. Indeed, effective iodine concentrations can be reached with hypotonic solutions. It may thus be desirable to make up the solution's tonicity by the addition of plasma cations so as to reduce the toxicity contribution that derives from the imbalance effects following bolus injection. Such cations will desirably be included in the ranges suggested in WO 90/01194 and WO 91/13636.

In particular, addition of sodium and calcium ions to provide a contrast medium isotonic with blood for all iodine concentrations is desirable and obtainable. The plasma cations may be provided in the form of salts with physiologically tolerable counterions, e.g. chloride, sulphate, phosphate, hydrogen carbonate etc., with plasma anions preferably being used.

The contrast media containing compounds of formula (I) can be administered by injection or infusion, e.g. by intervascular administration. Alternatively, contrast media containing compounds of formula (I) may also be administered orally. For oral administration the contrast medium may be in the form of a capsule, tablet or as liquid solution.

In a further embodiment the invention provides diagnostic agents comprising a compound of formula (I) and diagnostic compositions comprising a compound of formula (I) together with pharmaceutically acceptable carriers or excipients. The diagnostic agents and composition are preferably for use in X-ray diagnosis.

Hence, the invention further embraces use of a diagnostic agent and a diagnostic composition containing a compound of formula (I) in X-ray contrast examinations and use of a compound of formula (I) for the manufacture of a diagnostic composition for use as an X-ray contrast agent.

A method of diagnosis comprising administration of compounds of formula (I) to the human or animal body, examining the body with a diagnostic device and compiling data from the examination is also provided. In the method of diagnosis the body may also be preadministrated with compounds of formula (I).

Furthermore, a method of imaging, specifically X-ray imaging is provided, which comprises administration of compounds of formula (I) to the human or animal body, examining the body with a diagnostic device and compiling data from the examination and optionally analysing the data. In the method of imaging the body may also be preadministrated with compounds of formula (I).

Preparation

The compounds of the general formula (I) can be synthesized by multistep procedures from starting materials that are either known from the state of art or that are commercially available or can readily be produced from commercially available materials.

Compounds of formula (I) and (II) can be synthesized according to the general procedure of Scheme (1) below:

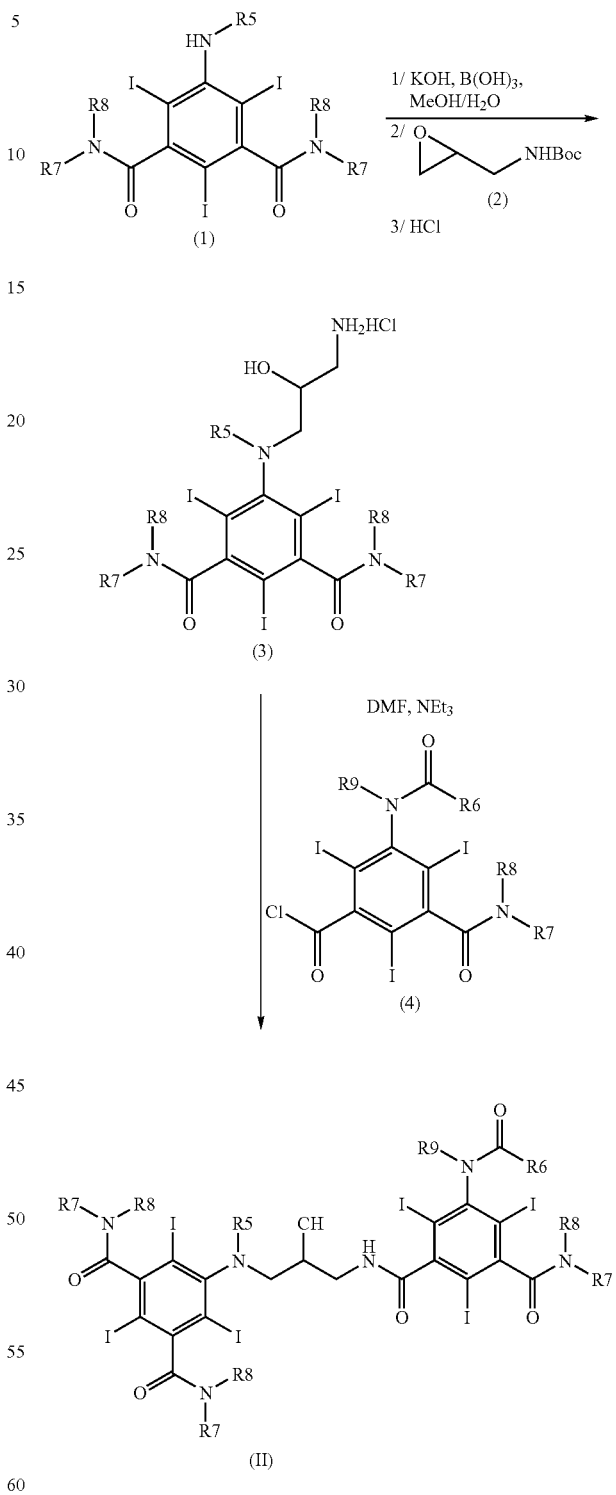

The triiodoarene (1) is reacted with tert-butyl-N-(2-oxiranylmethyl) carbamate (2) (commercially available from Aldrich). Deprotection of the primary amine of the monomer will lead to the desired free amine (3) which could be reacted with various acyl chloride such as (4). Finally full deprotection should provide the desired dimer (II).

PREPARATION OF INTERMEDIATES

Preparation A

5-Amino-2,4,6-triiodo-isophthaloyl dichloride was dissolved in dimethyl acetamide (DAMc) and a solution of acetoxyacetylchloride (2 eq) in DMAc was slowly added with efficient stirring. The reaction mixture was stirred overnight and the following day, the mixture was slowly poured into stirred ice water. The precipitate was filtered off and dried to give the desired material.

Following this procedure various compounds can be prepared, including but not limited to:

Acetic acid (3,5-bis-chlorocarbonyl-2,4,6-triiodo-phenylcarbamoyl)-methyl ester

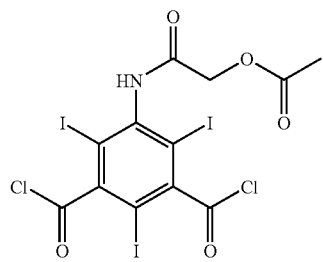

The structure was confirmed by $^1$H NMR (CDCl$_3$, 300 MHz): 10.43 (br s, 1H); 4.71 (s, 2H); 2.11 (s, 3H)

Acetic acid 2-acetoxy-1-(3,5-bis-chlorocarbonyl-2,4,6-triiodo-phenylcarbamoyl)-ethyl ester

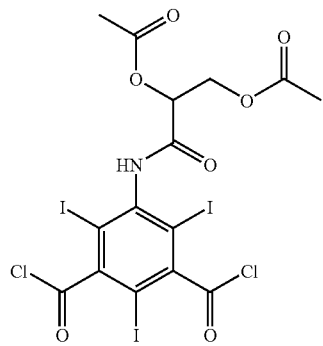

The structure was confirmed by $^1$H NMR (CDCl$_3$, 300 MHz): 10.45 (br s, 1H); 4.49-4.30 (m, 3H); 2.13 (s, 6H).

Acetic acid 2,3-diacetoxy-1-(3,5-bis-chlorocarbonyl-2,4,6-triiodo-phenylcarbamoyl)-propyl ester

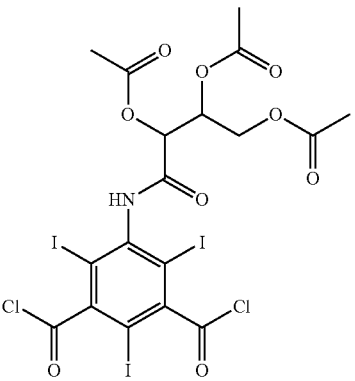

The structure was confirmed by $^1$H NMR (CDCl$_3$, 300 MHz): 8.08 (br s, 1H); 5.75-5.50 (m, 2H); 4.49-4.10 (m, 2H); 2.29 (s, 3H); 2.11 (s, 3H); 2.09 (s, 3H).

Preparation B

The bis-acid chloride from the previous step was dissolved in DMAC in a dry flask under a nitrogen atmosphere. Triethylamine (2 eq) was added to the solution immediately followed by the addition of 3-Methylamino-propane-1,2-diol (2 eq). After stirring overnight, the reaction mixture was concentrated to dryness, and the residue purified by chromatography using silica gel to give the desired product.

Following this procedure various compounds of formula (4) above can be prepared, including but not limited to:

Acetic acid {3-chlorocarbonyl-5-[(2,3-dihydroxy-propyl)-methyl-carbamoyl]-2,4,6-triiodo-phenylcarbamoyl}-methyl ester

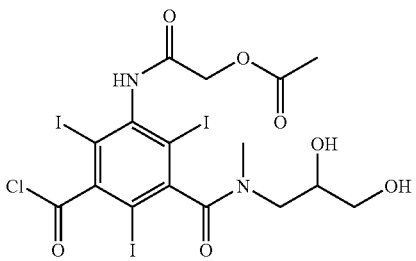

The structure was confirmed by $^1$H NMR (DMSO-D6, 300 MHz): 10.4 (br s, 1H); 4.70 (s, 2H); 3.89-3.83 (m, 1H);

3.75-3.67 (m, 1H); 3.51-3.42 (m, 2H); 3.25-3.15 (m, 1H); 2.85 (s, 3H); 2.15 (s, 3H)

Acetic acid 2-acetoxy-1-{3-chlorocarbonyl-5-[(2,3-dihydroxy-propyl)-methyl-carbamoyl]-2,4,6-triiodo-phenylcarbamoyl}-ethyl ester

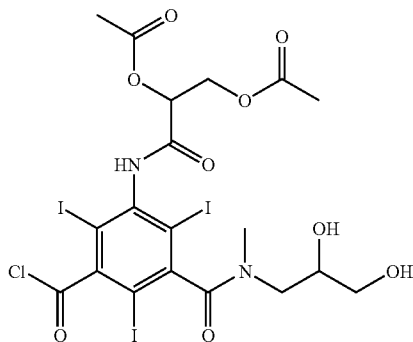

The structure was confirmed by $^1$H NMR (DMSO-D6, 300 MHz): 10.4 (br s, 1H); 4.70-4.65 (m, 3H); 3.89-3.83 (m, 1H); 3.75-3.67 (m, 1H); 3.51-3.42 (m, 2H); 3.25-3.15 (m, 1H); 2.85 (s, 3H); 2.15 (s, 6H).

Acetic acid 2,3-diacetoxy-1-{3-chlorocarbonyl-5-[(2,3-dihydroxy-propyl)-methyl-carbamoyl]-2,4,6-triiodo-phenylcarbamoyl}-propyl ester

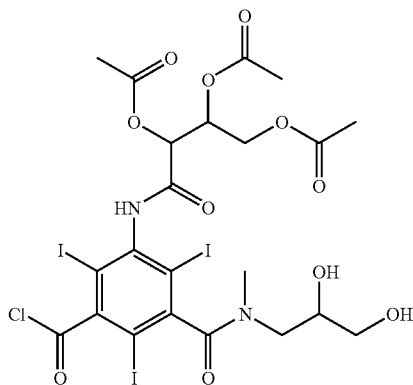

The structure was confirmed by $^1$H NMR (DMSO-D6, 300 MHz): 10.4 (br s, 1H); 5.63-5.60 (m, 2H); 4.40-4.05 (m, 2H); 4.0-2.60 (m, 2H); 3.46 (m, 2H); 3.30-3.05 (m, 1H); 2.85 (s, 3H); 2.26 (s, 3H); 2.08 (s, 3H); 2.02 (s, 3H).

Preparation C

Acetic acid (3,5-bis-chlorocarbonyl-2,4,6-triiodo-phenyl-carbamoyl)-methyl ester (20 g, 25.5 mmol) was dissolved in dry DMA (100 ml) and 2,2,-dimethyl-1,3-dioxolane-4-methanaine (6.62 ml, 51 mmol) was added. The reaction was stirred for 24 hours at room temperature under nitrogen. The reaction mixture was diluted with ethyl acetate and washed with ice-water (50 ml×3) and brine. The organics were collected, dried over MgSO$_4$, filtered and evaporated to give as a brown oil. This was purified by silica column chromatography eluting with petrol: ethyl acetate to give acetic acid {3-chlorocarbonyl-5-[(2,2-dimethyl-[1,3]dioxolan-4-ylmethyl)-carbamoyl]-2,4,6-triiodo-phenylcarbamoyl}-methyl ester (13.85 g, 17.5 mmol) as a pink solid.

Following this procedure various compounds of formula (4) above can be prepared, including but not limited to:

Acetic acid {3-chlorocarbonyl-5-[(2,2-dimethyl-[1,3]-dioxolan-4-ylmethyl)-carbamoyl]-2,4,6-triiodo-phenylcarbamoyl}-methyl ester

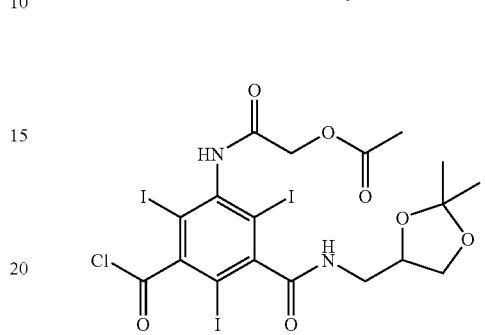

The structure was confirmed by Mass Spec (ESI) m/z: Calculated for $C_{18}H_{18}ClN_2O_7$ [M+H]$^+$ 791.520. Found 790.84. $^1$H NMR (DMSO; 300 MHz) δ=10.35-10.15 (m, 1H, NH), 9.03-8.87 (m, 1H, NH), 4.70 (s, 2H), 4.25 (m, 1H), 4.07 (m, 1H), 3.79 (m, 1H), 3.50-3.10 (m, 2H), 2.15 (s, 3H), 1.36 (s, 3H), 1.23 (s, 3H).

Acetic acid 2-acetoxy-1-[3-chlorocarbonyl-5-(2,3-dihydroxy-propylcarbamoyl)-2,4,6-triiodo-phenyl-carbamoyl]-ethyl ester

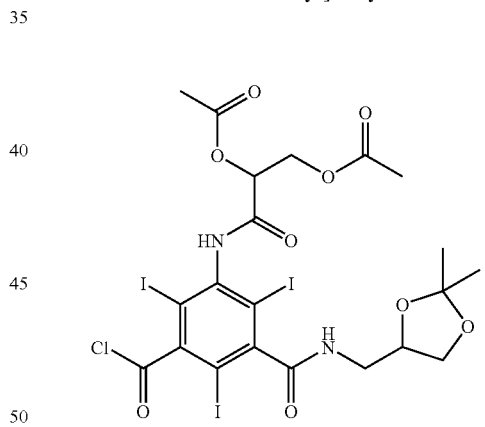

The structure was confirmed by Mass Spec (ESI) m/z: Calculated for $C_{21}H_{22}ClN_2O_9$ [M+H]$^+$ 863.594. Found 862.75. $^1$H NMR (CDCl$_3$; 300 MHz) δ=6.39 (s, br, 1H, NH), 5.63 (s, br, 1H, NH), 4.64 (m, 1H), 4.50 (m, 1H), 4.35 (m, 1H), 3.78-3.65 (m, 2H), 3.42 (m, 1H), 2.28 (d, 3H), 2.08 (s, 3H), (s, 3H), 1.43 (s, 3H), 1.33 (s, 3H)

Preparation D

5-Amino-2,4,6-triiodoisophthalic acid (50 g, 89.5 mol), readily available from Aldrich, was dissolved slowly in concentrated sulphuric acid (200 ml) at 50° C. The resulting purple solution was then added dropwise to formaldehyde (38% by weight, 100 ml) maintaining a temperature of between 40-50° C. The solution was stirred for 2 hours at 50°

C. and then allowed to cool. The mixture was poured onto ice water (3 L) and the solid was collected by filtration and dried in a vacuum oven at 50° C. for 7 days to give 2,4,6-triiododo-5-methylamino-isophthalic acid (55.3 g). Mass Spec (ESI) m/z: [M+H]$^+$=574.36. $^{13}$C NMR (DMSO; 300 MHz) δ=169.84, 152.75, 149.44, 90.49, 80.00, 35.55.

2,4,6-Triiododo-5-methylamino-isophthalic acid (50 g, 87.3 mmol) was stirred in thionyl chloride (275 ml, 1.41 mol) and DMF (1 ml) at 70° C. for 72 hours. The thionyl chloride was removed under reduced pressure and the resulting solid was partitioned between ethyl acetate (400 ml) and ice water (200 ml). The organic layer was collected, dried over MgSO$_4$, filtered and evaporated to dryness. The product was purified by silica column chromatography eluting with petrol:ethyl acetate to give 2,4,6-Triiodo-5-methylamino-isophthaloyl dichloride (30.93 g, 50.7 mmol).

Following this procedure various compounds can be prepared, including but not limited to:

2,4,6-Triiodo-5-methylamino-isophthaloyl dichloride

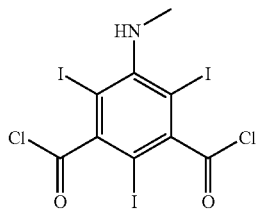

The structure was confirmed by $^{13}$C NMR (DMSO; 300 MHz) δ=169.42, 154.03, 149.85, 89.82, 75.23, 35.58.

Preparation E 2,4,6-Triiodo-5-methylamino-isophthaloyl dichloride (20 g, 32.8 mmol) was dissolved in DMA (60 ml) and acetoxyacetyl chloride (15.32 ml, 142 mmol) was added. The reaction was stirred overnight at room temperature with nitrogen bubbling through the reaction mixture. The reaction mixture was poured slowly onto ice-water (300 ml) and a white solid was isolated by filtration. The solid was dissolved in ethyl acetate and washed with water. The ethyl acetate was collected, dried over MgSO$_4$, filtered and evaporated to give a white solid. This was purified by silica column chromatography eluting with petrol:ethyl acetate to give acetic acid [(3,5-bis-chlorocarbonyl-2,4,6-triiodo-phenyl)-methyl-carbamoyl]-methyl ester (16.25 g, 22.9 mmol).

Following this procedure various compounds can be prepared, including but not limited to:

Acetic acid [(3,5-bis-chlorocarbonyl-2,4,6-triiodo-phenyl)-methyl-carbamoyl]-methyl ester

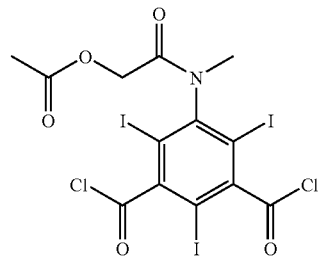

The structure was confirmed by Mass Spec (ESI) m/z: [M+H]$^+$=710.73. $^1$H NMR (CDCl$_3$; 300 MHz) δ=4.32 (s, 2H), 3.26 (s, 3H), 2.13 (s, 3H) $^{13}$C NMR (CDCl$_3$; 300 MHz) δ=170.11, 165.19, 151.89, 147.88, 95.91, 84.21, 62.39, 34.17, 20.47.

Preparation F

Acetic acid [(3,5-bis-chlorocarbonyl-2,4,6-triiodo-phenyl)-methyl-carbamoyl]-methyl ester (16.25 g, 22.9 mmol) and 3-methylamino-1,2,-propanediol (4.42 ml, 45.8 mmol) were stirred in DMA (80 ml) for 72 hours at room temperature. The mixture was diluted with ethyl acetate (150 ml) and washed with ice water/brine (50:50, 20 ml×3). The organics were collected, dried over MgSO$_4$, filtered and evaporated to dryness. The product was purified by silica column chromatography eluting with DCM: methanol to give acetic acid ({3-chlorocarbonyl-5-[(2,3-dihydroxy-propyl)-methyl-carbamoyl]-2,4,6-triiodo-phenyl}-methyl-carbamoyl)-methyl ester (5.42 g, 6.96 mmol).

Following this procedure various compounds of formula (4) above can be prepared, including but not limited to:

Acetic acid ({3-chlorocarbonyl-5-[(2,3-dihydroxy-propyl)-methyl-carbamoyl]-2,4,6-triiodo-phenyl}-methyl-carbamoyl)-methyl ester

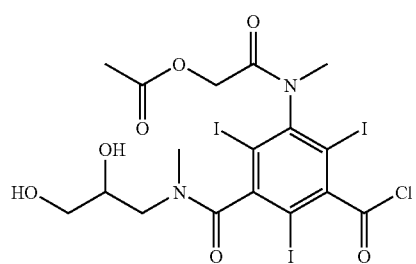

The structure was confirmed by Mass Spec (ESI) m/z: [M+H]$^+$=778.72.

Preparation G
N-(Hydroxyethyl)-Amino-2,3-propanediol

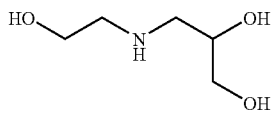

The commercially available glycidol (0.17 mol, 11 ml) was added dropwise to stirred ethanolamine (1 eq, 1.4 mol, 84.3 ml) at 0° C. Once addition was complete the reaction was allowed to warm up to room temperature, while stirring overnight. The product was then distilled (Ethanolamine first distilled at 60° C. at 1 Torr, and the desired product at 170° C. at 1 Torr). The product was obtained a clear oil that cooled to a clear viscous syrup (0.122 mol, yield=72%).

The structure was confirmed by $^{13}$C NMR (D$_2$O; 300 MHz) δ=50.21, 50.86, 60.36, 64.20, 70.63. $^1$H NMR (D$_2$O; 300 MHz) δ=2.55-2.75 (m, 4H) 3.45-3.7 (m, 4H) 3.75-3.85 (m, 1H)

Preparation H
2-[(2,2-Dimethyl-[1,3]-dioxolan-4-yl-methyl)-amino]-ethanol

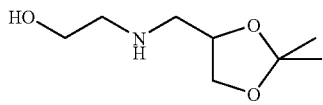

The N-(hydroxyethyl)-amino-2,3-propanediol (16.5 g, 122 mmol) was treated with a solution of HCl in dioxane (33.5 ml, 134 mmol). To this solution were added 2,2-dimethoxypropane (15.3 g, 147 mmol), DMAC (50 mL), and a catalytic amount of para-toluene sulphonic acid (0.006 mol, 1.16 g). The mixture stirred at room temperature for 24 hours. Triethylamine (1 mL) was then added, and the solvents removed by rotary evaporation. The viscous crude mixture was dissolved into triethylamine (30 mL) and ethyl acetate (500 mL) and stirred at RT for 30 min. The mixture was filtered and the collected solid washed several times with ethyl acetate. The filtrate was then evaporated on a high vacuum rotary evaporator at 40° C. to give a yellow liquid (0.122 mol, 99% yield).

The structure was confirmed by NMR. $^1$H NMR (D$_2$O; 300 MHz) δ=1.40 (s, 3H) 1.46 (s, 3H) 2.75-2.8 (m, 4H) 3.7-3.75 (m, 3H) 4.17 (dd, 1H) 4.37 (dd, 1H)

Preparation I
Acetic acid 2-acetoxy-1-{3-chlorocarbonyl-5-[(2,2-dimethyl-[1,3]-dioxolan-4-ylmethyl)-(2-hydroxy-ethyl)-carbamoyl]-2,4,6-triiodo-phenylcarbamoyl}-ethyl ester

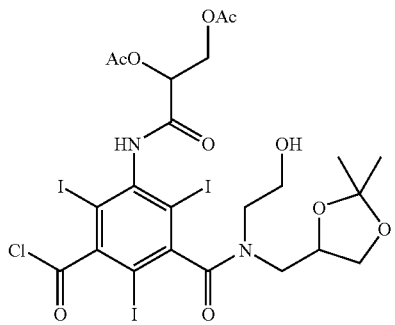

To a ice cooled solution of acetic acid 2-acetoxy-1-(3,5-bis-chlorocarbonyl-2,4,6-triiodo-phenylcarbamoyl)-ethyl ester (20 g, 0.026 mol) in anhydrous DMAC (20 ml) were added dropwise a solution of 2-[(2,2-Dimethyl-[1,3]dioxolan-4-yl-methyl)-amino]-ethanol (4.6 g, 0.026 mol) in DMAC (20 mL) followed by triethylamine (~3 g). The mixture was stirred at room temperature for 24 h and then poured over icewater (0.75 liter). A white precipitate formed. This was collected and washed with cold water. The filter cake was then dissolved in ethyl acetate and washed with brine. The organics were collected, dried over MgSO$_4$, filtered and evaporated to dryness. The product was purified by silica column chromatography eluting with Petroleum ether/ethyl acetate. Two peaks closely eluting at 80% ethyl acetate were analysed by NMR and mass spec, and show to both contain the desired material. These were combined post analysis to give the desired product (10 mmol, Yield=38%).

The structure was confirmed by Mass Spec (ESI) m/z: Calculated for $C_{23}H_{26}Cl\ I_3N_2O_{10}$ [M+H]$^+$ 906.64. Found 906.93. $^1$H NMR (CDCl$_3$; 300 MHz) δ=1.33 (2 s, 3H) 1.45 (2 s, 3H) 2.02 (s, 3H) 2.26 (s, 3H) 3-3.5 (m, 4H) 3.5-3.9 (m, 3H) 3.9-4.3 (m, 2H) 4.5 (m, 1H) 4.6-4.8 (m, 2H) 5.62 (NH singlet, 1H)

Following this procedure various compounds of formula (4) above can be prepared, including but not limited to:

Acetic acid {3-chlorocarbonyl-5-[(2,2-dimethyl-[1,3]-dioxolan-4-ylmethyl)-(2-hydroxy-ethyl)-carbamoyl]-2,4,6-triiodo-phenylcarbamoyl}-methyl ester

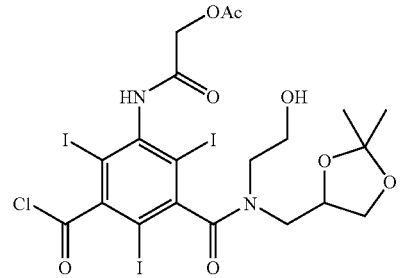

The structure was confirmed by Mass Spec (ESI) m/z: Calculated for $C_{20}H_{22}Cl\ I_3N_2O_8$ [M+H]$^+$ 834.57. Found 834.93. $^1$H NMR (CDCl$_3$; 300 MHz) δ=1.33 (2 s, 3H) 1.48 (2 s, 3H) 2.26 (s, 3H) 3-3.5 (m, 3H) 3.5-4.3 (m, 5H) 4.4 (m, 1H) 4.76 (1H NH)

Preparation J
(2-Hydroxy-1-hydroxymethyl-ethyl)-carbamic acid tert-butyl ester

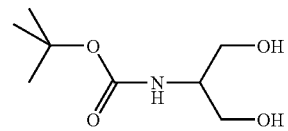

2-Amino-1,3-propanediol (5.0 g, 54.9 mmol) was dissolved in dry THF (175 ml) and triethylamine (7.7 ml) added. The solution was cooled in an ice-bath and di-tert-butylcarbonate (11.98 g, 54.9 mmol) added in portions over 15 mins. The solution was allowed to warm to ambient temperature and stirred for 90 mins. The solvent was evaporated and water (250 ml) added and the product extracted into ethyl acetate (4×125 ml). The combined organics were washed with brine, dried over magnesium sulphate, filtered and evaporated. The product was isolated by recrystallization from hot ethyl acetate-petrol (1:3) to give shiny flakes 5.18 g (49% yield).

The structure was confirmed by $^1$H NMR (300 MHz, CDCl$_3$): 1.44 (s, 9H), 3.08-3.17 (m, 1H), 3.61-3.84 (m, 4H).

Preparation K

Acetic acid 3-acetoxy-2-tert-butoxycarbonylamino-propyl ester

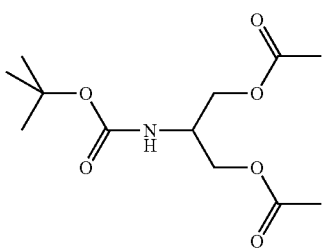

(2-Hydroxy-1-hydroxymethyl-ethyl)-carbamic acid tert-butyl ester (5.0 g, 26.1 mmol) was dissolved in pyridine (50 ml) and acetic anhydride (50 ml) was added. The solution was stirred at ambient temperature for 24 h when TLC showed no starting material remained. The solvent was evaporated and the residue dissolved in ethyl acetate (120 ml) and washed with dilute hydrochloric acid (3×50 ml), sodium bicarbonate solution (50 ml), brine, dried over magnesium sulphate, filtered and evaporated to give a colourless oil (7.2 g, 99% yield).

The structure was confirmed by $^1$H NMR (300 MHz, CDCl$_3$): 1.42 (s, 9H), 2.05 (s, 6H), 4.00-4.20 (m, 4H), 4.76-4.88 (m, 1H).

Preparation L

2-Acetoxy-1-acetoxymethyl-ethyl-ammonium trifluoroacetate

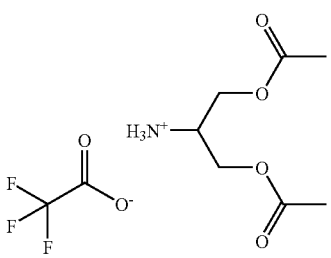

Acetic acid 3-acetoxy-2-tert-butoxycarbonylamino-propyl ester (7.2 g) was dissolved in trifluoroacetic acid (40 ml) and stirred at ambient temperature. Effervescence was rapid at the start and had stopped after 1 h when the volatiles were removed at reduced pressure to give the product as a viscous oil in quantitative yield.

The structure was confirmed $^1$H NMR (300 MHz, CDCl3): 2.12 (s, 9H), 3.83-3.91 (m, 1H), 4.27-4.46 (m, 4H).

Preparation M

Acetic acid 3-acetoxy-2-[3-(2-acetoxy-acetylamino)-5-chlorocarbonyl-2,4,6-triiodo-benzoylamino]-propyl ester

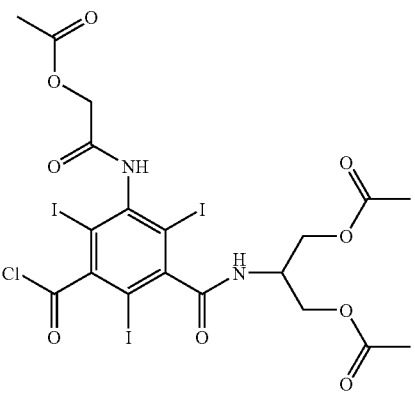

Acetic acid (3,5-bis-chlorocarbonyl-2,4,6-triiodo-phenylcarbamoyl)-methyl ester (4.82 g, 6.92 mmol) was added to a solution of 2-Acetoxy-1-acetoxymethyl-ethyl-ammonium trifluoroacetate (2.0 g, 6.92 mmol) in dimethylacetamide (30 ml) with triethylamine 2 ml, 15.8 mmol). The solution was heated at 40° C. for 18 h followed by 60° C. for 4 h. The reaction mixture was diluted with ethyl acetate (350 ml) and washed with ice-water (4×50 ml), brine (50 ml), dried over sodium sulphate, filtered and evaporated. The crude product was purified by chromatography on silica gel using ethyl acetate and petrol eluant to give the product as a white solid foam (1.11 g, 38% yield).

The structure was confirmed by Mass Spec (ESI) m/z: Calculated for $C_{19}H_{18}Cl\ I_3N_2O_9[M+H]^+$ 834.53. Found 834.84.

Preparation N (5-Amino-2,2-dimethyl-[1,3]dioxan-5-yl)-methanol

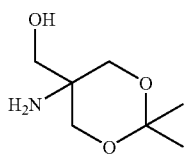

Tris hydrochloride (51 g, 324 mmol) was suspended in dry DMF (100 ml) and 2,2-dimethoxypropane (39 g, 374 mmol) was added followed by para-toluenesulfonic acid (2.6 g, 13.5 mmol). The mixture was stirred in a sealed flask for 18 h at ambient temperature when a clear solution resulted. Triethylamine (2.5 ml) was added and solvent evaporated. The viscous crude was dissolved in triethylamine (40 ml) and ethyl acetate (750 ml) added and the white precipitate of ammonium salts was filtered off after stirring for 30 mins. The filtrate was evaporated to give the product as a colourless liquid in approx. 85% yield.

The structure was confirmed by $^1$H NMR (300 MHz, CDCl$_3$): 1.38 (s, 3H), 1.41 (s, 3H), 3.48 (s, 2H), 3.53 (d, 2H) and 3.77 (d, 2H).

Preparation O

Acetic acid [3-chlorocarbonyl-5-(5-hydroxymethyl-2,2-dimethyl-[1,3]dioxan-5-ylcarbamoyl)-2,4,6-triiodo-phenylcarbamoyl]-methyl ester

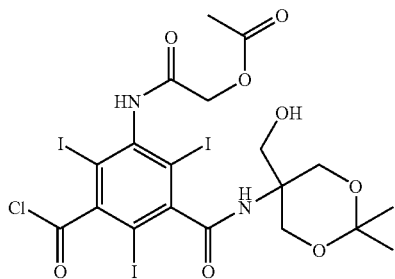

(5-Amino-2,2-dimethyl-[1,3]dioxan-5-yl)-methanol (9.5 g, 58.9 mmol) was dissolved in dimethylacetamide (100 ml) and triethylamine (2 ml) added. Acetic acid (3,5-bis-chlorocarbonyl-2,4,6-triiodo-phenylcarbamoyl)-methyl ester (21.0 g, 30.2 mmol) was added and the mixture heated under nitrogen at 60° C. for 24 h. On cooling, ethyl acetate (1.2 l) was added and the solution washed with ice-water (4×120 ml), brine, dried over sodium sulphate, filtered and evaporated to give the crude product. The pure product obtained as a white solid by chromatography on silica gel (8.32 g, 34% yield).

The structure was confirmed by Mass Spec (ESI) m/z: Calculated for C$_{19}$H$_{20}$Cl I$_3$N$_2$O$_8$[M+H]$^+$820.546. Found 818.89.

Preparation P

4-Dibenzylamino-butane-1,2,3-triol

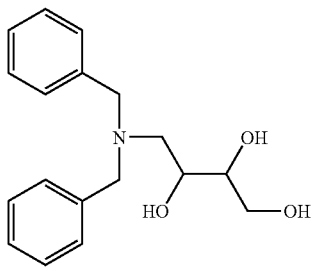

was prepared according to EP675105(B1)

Preparation Q

2-Dibenzylamino-1-(2,2-dimethyl-[1,3]-dioxolan-4-yl)-ethanol and {5-[(Dibenzylamino)-methyl]-2,2-dimethyl-[1,3]-dioxolan-4-yl}-methanol were prepared as a mixture

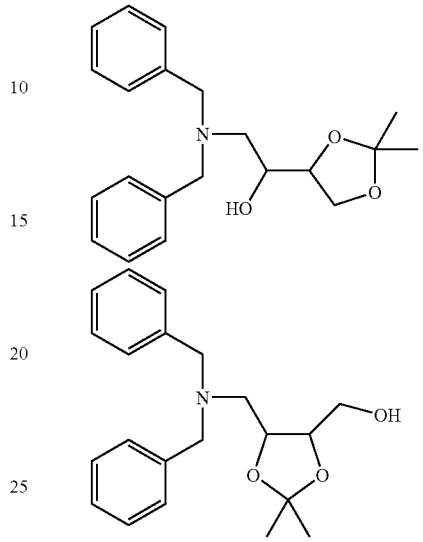

4-Dibenzylamino-butane-1,2,3-triol (10.0 g, 33.2 mmol) was dissolved in dry DMF (10 ml) and methanol (30 ml) and hydrogen chloride in dioxane (11 ml, 4N) was added. After 15 mins, methanol and excess hydrogen chloride were removed by evaporation at reduced pressure. Dimethoxypropane (4.0 g, 38.4 mmol) and para-toluenesulfonic acid (catalytic amount) were added and the mixture stirred for 18 h at ambient temperature. Triethylamine (0.5 ml) was added and solvents removed at reduced pressure. The residue did not dissolve in triethylamine (4-5 ml) so ethyl acetate (150 ml) was added and the solids filtered off. The filtrate was evaporated to give the crude product as an oil. The purified product mixture was obtained by chromatography on silica gel in combined yield of 8.18 g, 72%.

The structure was confirmed by Mass Spec (ESI) m/z: Calculated for C$_{21}$H$_{27}$NO$_3$ [M+H]$^+$ 341.454. Found 324.08.

Preparation R

Acetic acid {3-chlorocarbonyl-5-[2-(2,2-dimethyl-[1,3]-dioxolan-4-yl)-2-hydroxy-ethylcarbamoyl]-2,4,6-triiodo-phenylcarbamoyl}-methyl ester and Acetic acid {3-chlorocarbonyl-5-[(1,5-hydroxymethyl-2,2-dimethyl-[1,3]-dioxolan-4-ylmethyl)-carbamoyl]-2,4,6-triiodo-phenylcarbamoyl}-methyl ester were prepared as a mixture

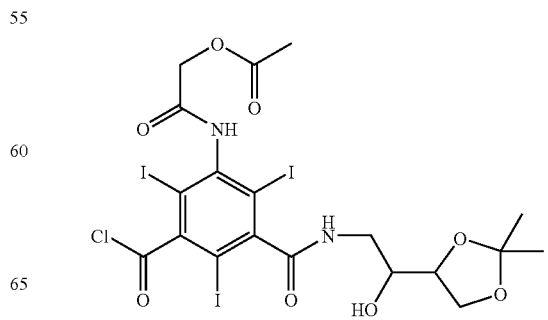

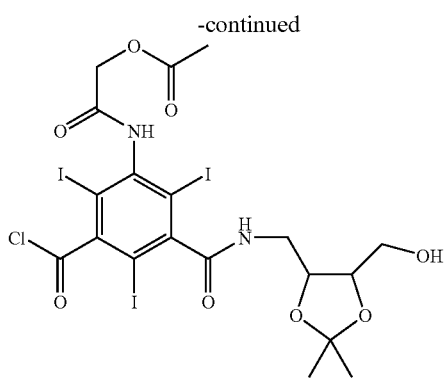

The mixture of 2-Dibenzylamino-1-(2,2-dimethyl-[1,3]dioxolan-4-yl)-ethanol and {5-[(Dibenzylamino)-methyl]-2,2-dimethyl-[1,3]dioxolan-4-yl}-methanol (2.32 g, 14.4 mmol) was dissolved in dimethylacetamide and triethylamine (4 ml, 28.8 mmol) added, followed by acetic acid (3,5-bis-chloro-carbonyl-2,4,6-triiodo-phenylcarbamoyl)-methyl ester (10.0 g, 14.4 mmol). The mixture was stirred at 40° C. for 24 h then cooled, diluted with ethyl acetate (150 ml) and washed with ice-water (4×30 ml), brine, dried over sodium sulphate, filtered and evaporated to give crude product as a solid foam. Pure product was obtained by chromatography on silica gel as a white solid foam (4.9 g, 42% yield).

The structure was confirmed by Mass Spec (ESI) m/z: Calculated for $C_{19}H_2Cl\ I_3N_2O_8[M+H]^+$ 820.546. Found 818.88.

Preparation S

5-Acetylamino-N,N'-bis-(2,3-dihydroxy-propyl)-2,4,6-triiodo-isophthalamide

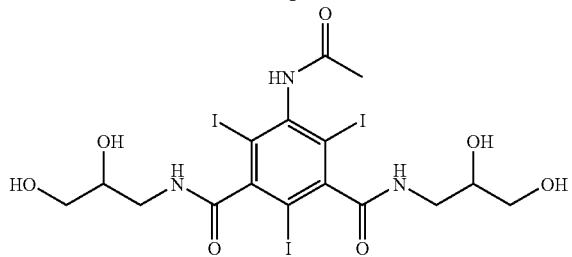

was prepared according to the U.S. Pat. No. 5,705,692

Preparation T

5-[Acetyl-(3-amino-2-hydroxy-propyl)-amino]-N,N'-bis-(2,3-dihydroxy-propyl)-2,4,6-triiodo-isophthalamide

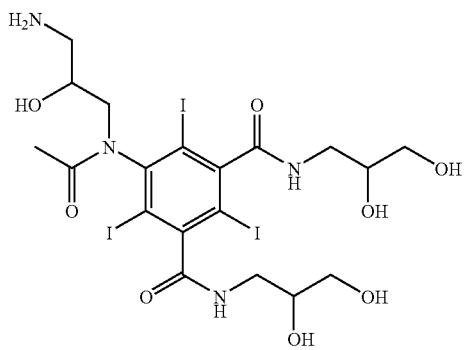

To a stirred solution of Water/tBuOH (2:1, 8 mL:10 mL) and KOH (0.73 g, 13 mmol, 1.2 eq was added at 40° C. 5-Acetylamino-N,N'-bis-(2,3-dihydroxy-propyl)-2,4,6-triiodo-isophthalamide (8.1 g, 11 mmol). To the clear solution was then added boric acid (0.47 g, 8 mmol, 0.7 eq). The mixture was cooled to room temperature and the pH adjusted to pH 12.6-13.0 with KOH. t-Butyl n-(2-oxiranyl-methyl) carbamate (0.996 g, 8 mmol, 0.7 eq) was added, and the pH was measured several times and adjusted to 12.6-13.0. The mixture was stirred over the weekend. An aqueous solution of HCl was then added until pH 4. The reaction mixture was evaporated to dryness. The product was purified by C18 column chromatography eluting with MeOH/Water to give 5-[Acetyl-(3-amino-2-hydroxy-propyl)-amino]-N,N'-bis-(2,3-dihydroxy-propyl)-2,4,6-triiodo-isophthalamide (2.09 mmol, Yield=19%).

The structure was confirmed by Mass Spec (ESI) m/z: Calculated for $C_{19}H_{27}I_3N_4O_8$ $[M+H]^+$ 820.162. Found 820.89.

Preparation U

5-[Acetyl-(3-amino-2-hydroxy-propyl)-amino]-N-(2,2-dimethyl-[1,3]-dioxolan-4-ylmethyl)-N'-(dimethyl-[1,3]-dioxolan-4-ylmethyl)-2,4,6-triiodo-isophthalamide

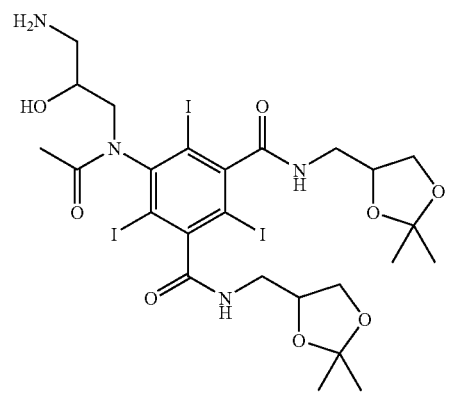

To a solution of 5-[Acetyl-(3-amino-2-hydroxy-propyl)-amino]-N,N'-bis-(2,3-dihydroxy-propyl)-2,4,6-triiodo-isophthalamide (14.6 g, 16 mmol) in dry DMF were added 2,2-dimethoxypropane (5 mL, 40 mmol, 2.5 eq) followed by a catalytic amount of p-toluene sulfonic acid (0.15 g, 1 mmol, 0.06 eq). the reaction mixture was stirred at room temperature over the week-end. Triethylamine (1 mL) was added, and the mixture was evaporated to dryness. The crude mixture was used without purification into the next step.

The structure was confirmed by Mass Spec (ESI) m/z: Calculated for $C_{25}H_{35}I_3N_4O_8$ $[M+H]^+$ 900.293. Found 901.04.

EXAMPLES

Example 1

5{[3-(3-Hydroxymethylamino-5-[(2,3-dihydroxypropyl)aminocarbonyl]-2,4,6-triiodobenzoylamino)-2-hydroxypropyl]-acetyl-amino}-N,N'-bis-(2,3-dihydroxy-propyl)-2,4,6-triiodo-isophthalamide

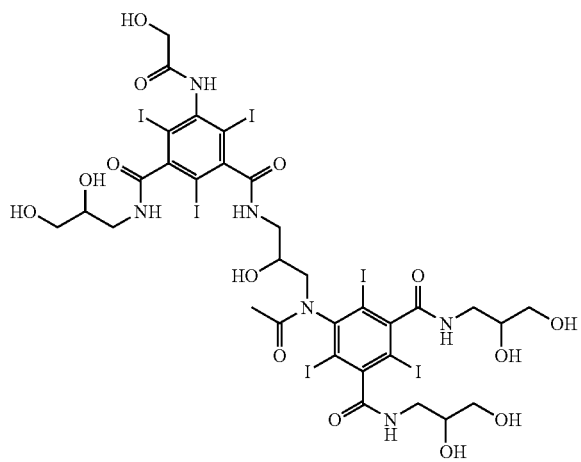

To a solution of 5-[Acetyl-(3-amino-2-hydroxy-propyl)-amino]-N-(2,2-dimethyl-[1,3]dioxolan-4-ylmethyl)-N'-(dimethyl-[1,3]dioxolan-4-ylmethyl)-2,4,6-triiodo-isophthalamide (2.0 g, 2 mmol) in DMF (4 mL) were added triethylamine (0.45 g, 4 mmol, 2 eq) followed by acetic acid {3-chlorocarbonyl-5-[(2,2-dimethyl-[1,3]dioxolan-4-ylmethyl)-carbamoyl]-2,4,6-triiodo-phenylcarbamoyl}-methyl ester (1.85 g, 2 mmol, 1 eq). The reaction mixture was stirred at room temperature overnight under nitrogen. The mixture was diluted with ethylacetate and washed with water. The organics were collected, dried over MgSO$_4$, filtered and evaporated to dryness. The product was purified by silica column chromatography eluting with ethylacetate/MeOH to give acetic acid {3-[3-(acetyl-{3,5-bis-[(2,2-dimethyl-[1,3]dioxolan-4-ylmethyl)-carbamoyl]-2,4,6-triiodo-phenyl}-amino)-2-hydroxy-propylcarbamoyl]-5-[(2,2-dimethyl-[1,3]dioxolan-4-ylmethyl)-carbamoyl]-2,4,6-triiodo-phenylcarbamoyl}-methyl ester (725 µmol, Yield=33%).

The structure was confirmed by Mass Spec (ESI) m/z: Calculated for $C_{43}H_{52}I_6N_6O_{15}[M+H]^+$ 1654.351. Found 1655.10.

Acetic acid {3-[3-(acetyl-{3,5-bis-[(2,2-dimethyl-[1,3]dioxolan-4-ylmethyl)-carbamoyl]-2,4,6-triiodo-phenyl}-amino)-2-hydroxy-propylcarbamoyl]-5-[(2,2-dimethyl-[1,3]dioxolan-4-ylmethyl)-carbamoyl]-2,4,6-triiodo-phenylcarbamoyl}-methyl ester (1.2 g, 725 µmol) was refluxed in MeOH/2M HCl (1:1, 5 mL:5 mL) for 1 hour. The reaction was then concentrated to dryness and the crude material purified by R-HPLC to give the desired product.

The structure was confirmed by Mass Spec (ESI) m/z: Calculated for $C_{32}H_{32}I_6N_6O_{14}$ [M+H]$^+$ 1492.118. Found 1493.11.

Following this procedure various compounds of formula (II) above can be prepared, including but not limited to:

Example 2

5{[3-(3,4-dihydroxyethylamino-5-[(2,3-dihydroxypropyl)aminocarbonyl]-2,4,6-triiodobenzoylamino)-2-hydroxypropyl]-acetyl-amino}-N,N'-bis-(2,3-dihydroxy-propyl)-2,4,6-triiodo-isophthalamide

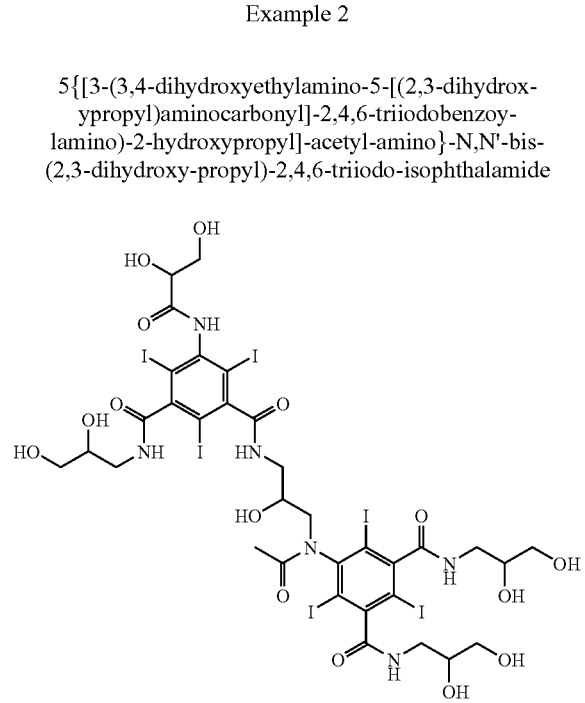

The structure was confirmed by Mass Spec (ESI) m/z: Calculated for $C_{33}H_{40}I_6N_6O_{15}[M+H]^+$ 1522.144. Found 1522.69.

Example 3

5{[3-(3-Hydroxymethylamino-5-[N'-(2,3-dihydroxypropyl)-N'-(2-hydroxyethyl)aminocarbonyl]-2,4,6-triiodobenzoylamino)-2-hydroxypropyl]-acetyl-amino}-N,N'-bis-(2,3-dihydroxy-propyl)-2,4,6-triiodo-isophthalamide The structure was confirmed by Mass Spec (ESI) m/z: Calculated for $C_{34}H_{42}I_6N_6O_{15}$ [M+H]$^+$ 1536.171. Found 1536.72.

Example 4

5{[3-(3,4-dihydroxyethylamino-5-[N'-(2,3-dihydrox-ypropyl)-N'-(2-hydroxyethyl)aminocarbonyl]-2,4,6-triiodobenzoylamino)-2-hydroxypropyl]-acetyl-amino}-N,N'-bis-(2,3-dihydroxy-propyl)-2,4,6-triiodo-isophthalamide

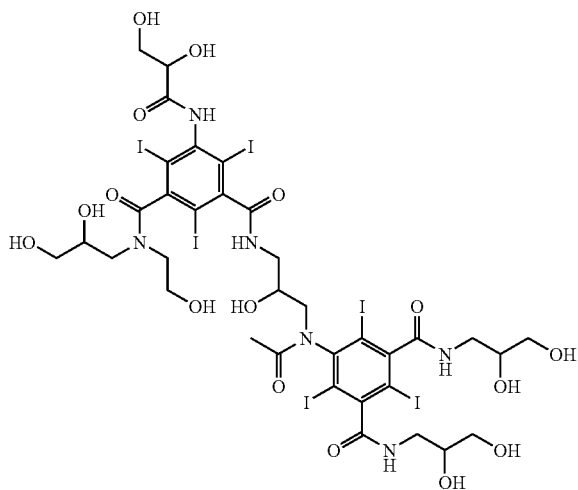

The structure was confirmed by Mass Spec (ESI) m/z: Calculated for $C_{35}H_{44}I_6N_6O_{16}$ $[M+H]^+$ 1566.198. Found 1566.69.

Example 5

5{[3-(3-Hydroxymethylamino-5-[(2,3-dihydroxypro-pyl)aminocarbonyl]-2,4,6-triiodobenzoylamino)-2-hydroxypropyl]-formyl-amino}-N,N'-bis-(2,3-dihy-droxy-propyl)-2,4,6-triiodo-isophthalamide

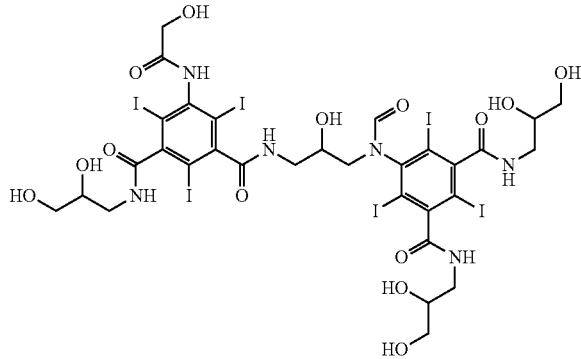

The structure was confirmed by Mass Spec (ESI) m/z: Calculated for $C_{31}H_{36}I_6N_6O_{14}$ 1477.6. found 1478.7.

What is claimed is:

1. Compounds of formula (I)

$$R^A-CO-N(R^2)-(CR^1{}_2)_n-N(R^5)-R^B \qquad \text{Formula (I)}$$

and salts or optical active isomers thereof, wherein each $R^1$ independently are the same or different and denotes a hydrogen atom, a hydroxyl group, a $C_1$ to $C_4$ straight of branched alkyl group or a $C_1$ to $C_4$ straight of branched oxyalkyl group;

$R^2$ denotes a hydrogen atom or a $C_1$ to $C_4$ straight of branched alkyl group;

$R^5$ denotes a group of formula $-CO-R^4$ where $R^4$ denotes a hydrogen atom or a $C_1$ to $C_4$ straight of branched alkyl group optionally substituted by 1 to 4 hydroxyl moieties;

$R^A$ and $R^B$ independently are the same or different and denote a triiodinated phenyl group; and n denotes a positive integer of 1 to 6.

2. Compound as claimed in claim 1 wherein each $R^1$ group independently denote hydrogen atoms or a hydroxyl groups.

3. Compound as claimed in claim 1 wherein the $R^2$ group denotes a hydrogen atom or a methyl group.

4. Compound as claimed in claim 1 wherein $R^5$ denotes one of the acyl groups of formula $-CHO$, $-COCH_3$, $-COCH_2-OH$ and $-CO-CHOH-CH_2-OH$.

5. Compound as claimed in claim 1 wherein $R^5$ denotes formyl or acetyl residues.

6. Compound as claimed in claim 1 wherein n denotes an integer of 2 to 5.

7. Compound as claimed in claim 1 wherein $R^A$ and $R^B$ independently are the same or different and denote a 2,4,6-triiodinated phenyl group further substituted by two groups $R^3$ in the 3 and 5 positions wherein each $R^3$ are the same or different and denote a hydrogen atom or a non-ionic hydrophilic moiety, provided that at least one $R^3$ group in the compound of formula (I) is a hydrophilic moiety.

8. Compound as claimed in claim 7 wherein each $R^3$ may be the same or different and denotes a non-iconic hydrophilic moiety comprising esters, amides and amine moieties, optionally further substituted by a straight chain or branched chain $C_{1-10}$ alkyl groups, where the alkyl groups also may have one or more $CH_2$ or CH moieties replaced by oxygen or nitrogen atoms and may further contain one or more groups selected from oxo, hydroxyl, amino or carboxyl derivative, and oxo substituted sulphur and phosphorus atoms.

9. Compound as claimed in claim 8 wherein the $R^3$ substituents are the same or different and are polyhydroxy $C_{1-5}$ alkyl, hydroxyalkoxyalkyl with 1 to 5 carbon atoms and hydroxypolyalkoxyalkyl with 1 to 5 carbon atoms, and are attached to the iodinated phenyl group via an amide or a carbamoyl linkage.

10. Compound as claimed in claim 9 wherein the $R^3$ substituents are the same or different and selected from the group:
- $-CONH-CH_2-CH_2-OH$;
- $-CONH-CH_2-CHOH-CH_2-OH$;
- $-CON(CH_3)CH_2-CHOH-CH_2OH$;
- $-CONH-CH-(CH_2{}^{-OH})_2$;
- $-CON-(CH_2-CH_2-OH)_2$;
- $-CONH_2$;
- $-CONHCH_3$;
- $-NHCOCH_2OH$;
- $-N(COCH_3)H$;
- $-N(COCH_3)C_{1-3}$ alkyl;
- $-N(COCH_3)$-mono, bis or tris-hydroxy $C_{1-4}$ alkyl;
- $-N(COCH_2OH)$-hydrogen, mono, bis or tris-hydroxy $C_{1-4}$ alkyl;
- $-N(CO-CHOH-CH_2OH)$-hydrogen, mono, bis or tri-hydroxylated $C_{1-4}$ alkyl;
- $-N(CO-CHOH-CHOH-CH_2OH)$-hydrogen, mono, bis or trihydroxylated $C_{1-4}$ alkyl-$N(COCH_2OH)_2$;
- $-CON(CH_2-CHOH-CH_2-OH)(CH_2-CH_2-OH)$
- $-CONH-C(CH_2-OH)_3$; and
- $-CONH-CH(CH_2-OH)(CHOH-CH_2-OH)$.

11. Compound as claimed in claim 10 wherein the $R^3$ groups are the same or different and selected from the following group: —CONH—CH$_2$—CHOH—CH$_2$—OH; —CON(CH$_3$)CH$_2$—CHOH—CH$_2$OH; —CONH—CH—(CH$_2$—OH)$_2$; —CON—(CH$_2$—CH$_2$—OH)$_2$; —CON(CHOH—CH$_2$—OH)(CH$_2$—CH$_2$OH); —NH—COCH$_2$OH, —NH—CO—CHOH—CH$_2$OH; and —NH—CO—CHOH—CHOH—CH$_2$OH.

12. Compound as claimed in claim 1 of formula (II)

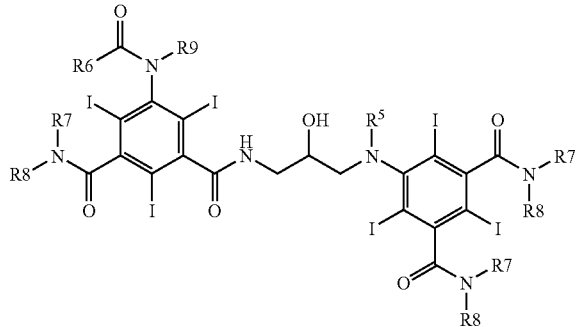

(II)

wherein R$^6$ represents a moiety —CH$_2$—OH, —CHOH—CH$_2$—OH or CHOH—CHOH—CH$_2$—OH;

R$^9$ represents a H, —CH$_3$, —CH$_2$—CH$_2$—OH or —CH$_2$—CH(OH)—CH$_2$—OH; each of R$^7$ and R$^8$ are the same or different and represents H, —CH$_3$, —CH$_2$—CH$_2$—OH or —CH$_2$—CH(OH)—CH$_2$—OH; and R$^5$ denotes formyl or acetyl residues.

13. Compound as claimed in claim 1 being selected from the following:

5{[3-(3-Hydroxymethylamino-5-[(2,3dihydroxypropyl)aminocarbonyl]-2,4,6-triiodobenzoylamino)-2-hydroxypropyl]-acetyl-amino}-N,N'-bis-(2,3-dihydroxy-propyl)-2,4,6-triiodo-isophthalamide;

5{[3-(3,4-dihydroxyethylamino-5-[(2,3-dihydroxypropyl)aminocarbonyl]-2,4,6-triiodobenzoylamino)-2-hydroxypropyl]-acetyl-amino}-N,N'-bis-(2,3-dihydroxypropyl)-2,4,6-triiodo-isophthalamide;

5{[3-(3-Hydroxymethylamino-5-[N'-(2,3-dihydroxypropyl)-N'-(2-hydroxyethyl)aminocarbonyl]-2,4,6-triiodobenzoylamino)-2-hydroxypropyl]-acetyl-amino}-N,N'-bis-(2,3-dihydroxy-propyl)-2,4,6-triiodo-isophthalamide;

5{[3-(3,4-dihydroxyethylamino-5-[N'-(2,3-dihydroxypropyl)-N'-(2-hydroxyethyl)aminocarbonyl]-2,4,6-triiodobenzoylamino)-2-hydroxypropyl]-acetyl-amino}-N,N'-bis-(2,3-dihydroxy-propyl)-2,4,6-triiodo-isophthalamide; and 5{[3-(3-Hydroxymethylamino-5-[(2,3-dihydroxypropyl)aminocarbonyl]-2,4,6-triiodobenzoylamino)-2-hydroxypropyl]-formyl-amino}-N,N'-bis-(2,3-dihydroxy-propyl)-2,4,6-triiodo-isophthalamide.

14. A composition comprising a compound of formula (I) as claimed in claim 1 together with a pharmaceutically acceptable carrier or excipient.

15. A composition comprising compound of formula (II) as claimed in claim 12 together with a pharmaceutically acceptable carrier or excipient.

16. A method of imaging, comprising administration of compounds of formulas (I) as defined in claim 1 to the human or animal body, examining the body with a diagnostic device and compiling data from the examination and optionally analysing the data.

17. A method of imaging, comprising administration of compounds of formulas (II) as defined in claim 12 to the human or animal body, examining the body with a diagnostic device and compiling data from the examination and optionally analysing the data.

* * * * *